United States Patent
Fehr et al.

(10) Patent No.: US 9,044,316 B2
(45) Date of Patent: Jun. 2, 2015

(54) INSTALLATION AND SEALING OF A BATTERY ON A THIN GLASS WAFER TO SUPPLY POWER TO AN INTRAOCULAR IMPLANT

(75) Inventors: Jean-Noel Fehr, Roanoke, VA (US); Alain Saurer, Roanoke, VA (US); Andreas Schlappi, Roanoke, VA (US)

(73) Assignee: ELENZA, INC., Roanoke, VA (US)

( * ) Notice: Subject to any disclaimer, the term of this patent is extended or adjusted under 35 U.S.C. 154(b) by 0 days.

(21) Appl. No.: 13/821,383

(22) PCT Filed: Sep. 6, 2011

(86) PCT No.: PCT/US2011/050533
§ 371 (c)(1),
(2), (4) Date: Jun. 3, 2013

(87) PCT Pub. No.: WO2012/033752
PCT Pub. Date: Mar. 15, 2012

(65) Prior Publication Data
US 2013/0245755 A1    Sep. 19, 2013

Related U.S. Application Data

(60) Provisional application No. 61/380,342, filed on Sep. 7, 2010.

(51) Int. Cl.
*A61F 2/16*   (2006.01)
*A61F 2/14*   (2006.01)
*H01M 2/10*   (2006.01)

(52) U.S. Cl.
CPC .............. *A61F 2/16* (2013.01); *H01M 2/1022* (2013.01); *A61F 2/1624* (2013.01); *A61F 2/14* (2013.01)

(58) Field of Classification Search
CPC .......... G02C 7/085; G02B 3/14; A61F 2/1624
USPC ................................................ 623/6.11, 6.22
See application file for complete search history.

(56) References Cited

U.S. PATENT DOCUMENTS 4,300,818 A    11/1981 Schachar
4,309,603 A    1/1982 Stauffer
(Continued)

FOREIGN PATENT DOCUMENTS

WO    WO/2011/063080    12/2011

OTHER PUBLICATIONS

International Search Report in connection with international application No. PCTUS2011/050533; dtd Jan. 5, 2012.

(Continued)

*Primary Examiner* — Evan Pert
(74) *Attorney, Agent, or Firm* — Foley & Lardner LLP (57) ABSTRACT

Many modern implantable ophthalmic devices include electronic components, such as electro-active cells, that can leak harmful substances into the eye and/or surrounding tissue. In the implantable ophthalmic devices disclosed herein, electronic components are hermetically sealed to facilitate mechanically connecting components of an implantable ophthalmic device. Furthermore, the device includes at least one battery with a surface comprising electrical contact portions, a housing for the at least one battery, a first wafer bonded to the housing such that the housing and the first wafer form a hermetically sealed surface around the battery, and an electronic circuit electrically connected to the electrical contact portions of the battery.

32 Claims, 10 Drawing Sheets

(56) References Cited

U.S. PATENT DOCUMENTS

| | | | |
|---|---|---|---|
| 4,373,218 A | 2/1983 | Schachar | |
| 4,466,703 A | 8/1984 | Nishimoto | |
| 4,601,545 A | 7/1986 | Kern | |
| 4,787,903 A | 11/1988 | Grendahl | |
| 5,066,301 A | 11/1991 | Wiley | |
| 5,653,751 A | 8/1997 | Samiy et al. | |
| 5,712,721 A | 1/1998 | Large | |
| 6,200,342 B1 | 3/2001 | Tassignon | |
| 6,282,449 B1 | 8/2001 | Kamerling et al. | |
| 6,619,799 B1 | 9/2003 | Blum et al. | |
| 6,638,304 B2 | 10/2003 | Azar | |
| 6,706,066 B1 | 3/2004 | Zhou et al. | |
| 6,790,232 B1 | 9/2004 | Lang | |
| 7,001,427 B2 * | 2/2006 | Aharoni et al. | 623/4.1 |
| 7,041,133 B1 | 5/2006 | Azar | |
| 7,524,577 B2 | 4/2009 | Bates | |
| 7,727,277 B2 * | 6/2010 | Aharoni et al. | 623/6.22 |
| 7,736,390 B2 * | 6/2010 | Aharoni et al. | 623/6.13 |
| 7,776,087 B2 * | 8/2010 | Aharoni et al. | 623/6.11 |
| 7,926,940 B2 | 4/2011 | Blum et al. | |
| 7,964,833 B2 | 6/2011 | Holladay | |
| 2004/0220643 A1 | 11/2004 | Schmidt | |
| 2006/0206205 A1 | 9/2006 | Azar | |
| 2007/0139001 A1 | 6/2007 | Hahn | |
| 2009/0204207 A1 | 8/2009 | Blum et al. | |
| 2009/0255324 A1 | 10/2009 | Ishibashi et al. | |
| 2013/0245754 A1 * | 9/2013 | Blum et al. | 623/6.13 |

OTHER PUBLICATIONS

International Preliminary Report on Patentability issued in International Application No. PCT/US2011/050533 issued Mar. 12, 2013.

* cited by examiner

INSTALLATION AND SEALING OF A BATTERY ON A THIN GLASS WAFER TO SUPPLY POWER TO AN INTRAOCULAR IMPLANT

CROSS REFERENCE TO RELATED APPLICATIONS

This application is a National Stage entry of International Application No. PCT/US2011/050533 filed on Sep. 6, 2011, which claims the benefit of U.S. Provisional Application No. 61/380,342, filed Sep. 7, 2010 and entitled "Installation and Sealing of a Battery on a Thin Glass Wafer to Supply Power to an Intraocular Implant", the disclosures of which are incorporated herein by reference in their entireties.

BACKGROUND OF THE INVENTION

The present invention relates generally to implantable ophthalmic devices to assist in vision correction. Standard tools for correction of various vision defects such as presbyopia include reading glasses, multifocal ophthalmic lenses, and contact lenses fit to provide monovision. Some vision correction techniques involve implanting a form of lens into the eye itself. For example, Pseudophakia is the replacement of the crystalline lens of the eye with an intra-ocular lense (IOL), usually following surgical removal of the crystalline lens during cataract surgery. In a pseudophakic individual, the absence of the crystalline lens causes a complete loss of accommodation that results in an inability to focus on either near or intermediate distance objects.

Conventional IOLs are monofocal, spherical lenses that provide focused retinal images for far objects (e.g., objects over two meters away). Generally, the focal length (or optical power) of a spherical IOL is chosen based on viewing a far object that subtends a small angle (e.g., about seven degrees) at the fovea. Unfortunately, because monofocal IOLs have a fixed focal length, they are not capable of mimicking or replacing the eye's natural accommodation response. Ophthalmic devices with electro-active elements, such as liquid crystal cells, can be used to provide variable optical power as a substitute for the accommodation of an damaged or removed crystalline lens. For example, electro-active elements can be used as shutters that provide dynamically variable optical power as disclosed in U.S. Pat. No. 7,926,940 to Blum et al., which is incorporated herein by reference in its entirety. IOLs with electro-active elements and other electronic components must be well sealed to prevent potentially foreign substances, such as the liquid crystal materials used in the electro-active elements, from leaking into the eye and surrounding tissue.

Furthermore, cavities of the IOL that contain electrical components must be properly sealed such that no bodily fluid from the ocular region will be able to interfere with the functionality of the electrical components. Additionally, the system and methods of sealing electrical components of the IOL must be durable over a long period of time. To date, IOLs with electro-active elements and other electronic components have been made by potting or encapsulating the components in a shell of epoxy, polyurethane, or another suitable type of curable compound. However, potting compounds do not always adhere well to the biocompatible metals used for electrical connections in IOLs. Potting compounds may also degrade over an IOL's expected lifetime, which can be twenty years or more.

SUMMARY OF THE DISCLOSED EMBODIMENTS

According to one exemplary embodiment, a system for electrically and mechanically connecting components of an implantable ophthalmic device to provide a bio-compatible sealing to prevent the ingress of fluid and the egress of battery fluids is disclosed. The system includes at least one battery with a surface comprising electrical contact portions, a housing for the at least one battery, a first wafer bonded to the housing such that the housing and the first wafer form a sealed surface around the battery, and an electronic circuit electrically connected to the electrical contact portions of the battery.

According to another exemplary embodiment, a system for electrically and mechanically connecting components of an implantable ophthalmic device to provide a bio-compatible sealing to prevent the ingress of fluid and the egress of battery fluids is disclosed. The system includes at least one battery with a surface comprising electrical contact portions, a first wafer having a first cavity the at least one battery is inserted into and a second wafer bonded to the first wafer using a laser fusion bonding process such that the first wafer and the second wafer form a sealed cavity around the battery. The system also includes an electrical circuit that is directly connected to the electrical contact portions of the battery wherein the electrical circuit is inserted into a gap in a third wafer and an inductive coil inserted into a second cavity of the first wafer wherein the inductive coil is placed on a surface of the third wafer.

According to yet another exemplary embodiment, a method of manufacturing an implantable ophthalmic device to prevent the ingress of fluid into a cavity of the device is disclosed. The includes the steps of placing at least one battery with a surface comprising electrical contact portions into a housing, bonding the housing with a first wafer such that the housing and the first wafer form a hermetically sealed cavity around the battery and placing the first wafer in a position such that an integrated circuit is electrically connected to the electrical contact portions of the battery.

BRIEF DESCRIPTION OF THE DRAWINGS

The accompanying drawings, which are incorporated in and constitute a part of this specification, illustrate embodiments of the invention and together with the description serve to explain principles of the invention.

DETAILED DESCRIPTION OF THE PREFERRED EMBODIMENTS

Implantable ophthalmic devices, such as intraocular lenses are typically implanted in the eye to serve as permanent or quasi-permanent correction for pseudophakia, aphakia, and other conditions affecting a patient's vision. Illustrative implantable ophthalmic devices may be inserted or implanted in the anterior chamber or posterior chamber of the eye or within any anatomical structure of the eye. Because they are inserted or implanted into the eye itself, they should not leak or leach foreign materials, such as liquid crystal material or electrolytes used in batteries, into the eye or surrounding tissue. Otherwise, they could cause damage to the eye and/or tissue surrounding the eye.

Figure 1:
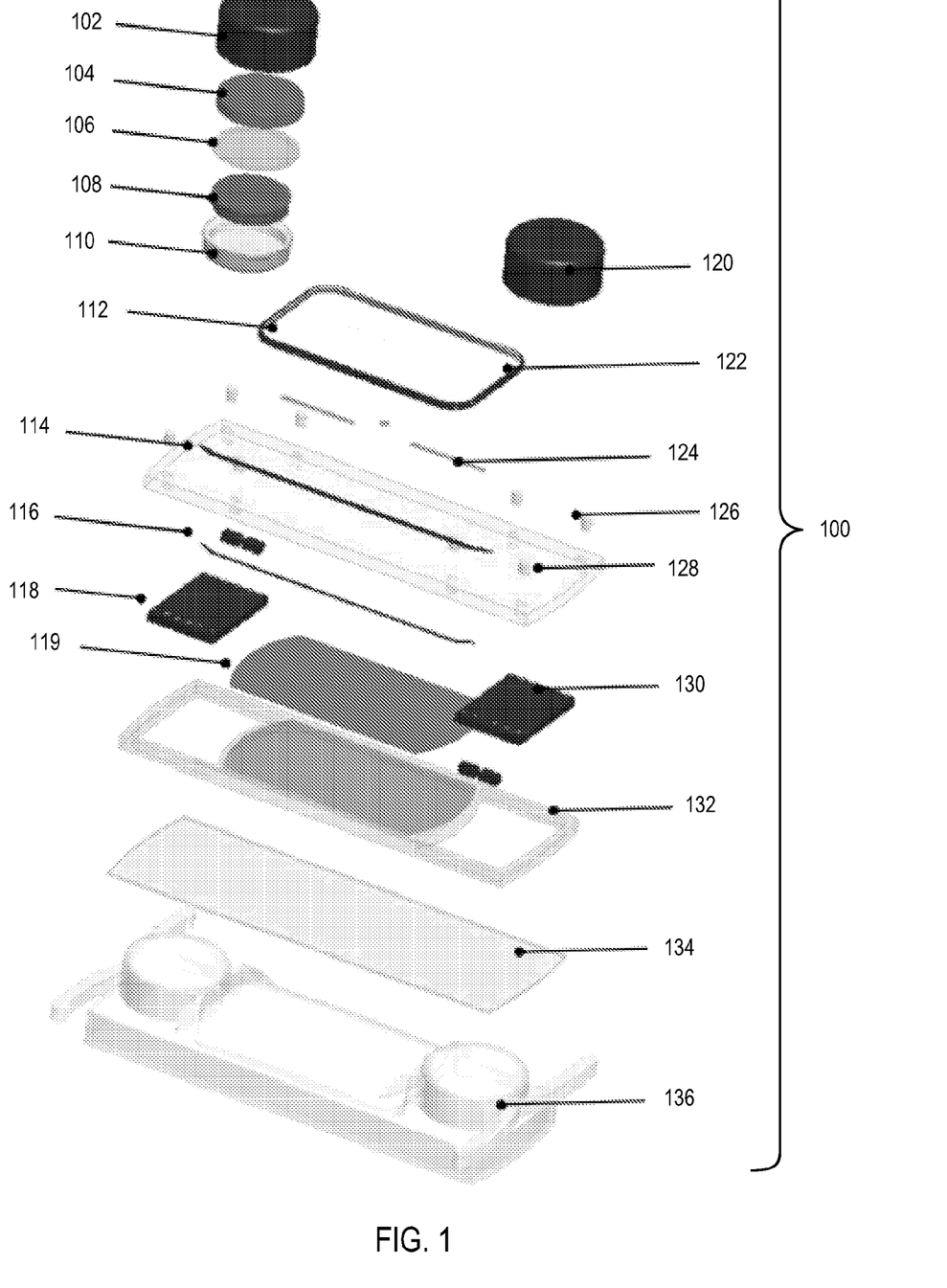
FIG. 1 is an exploded view of a hermetically sealed electronics assembly to be used in an implantable ophthalmic device according to one embodiment.
Figure 2:
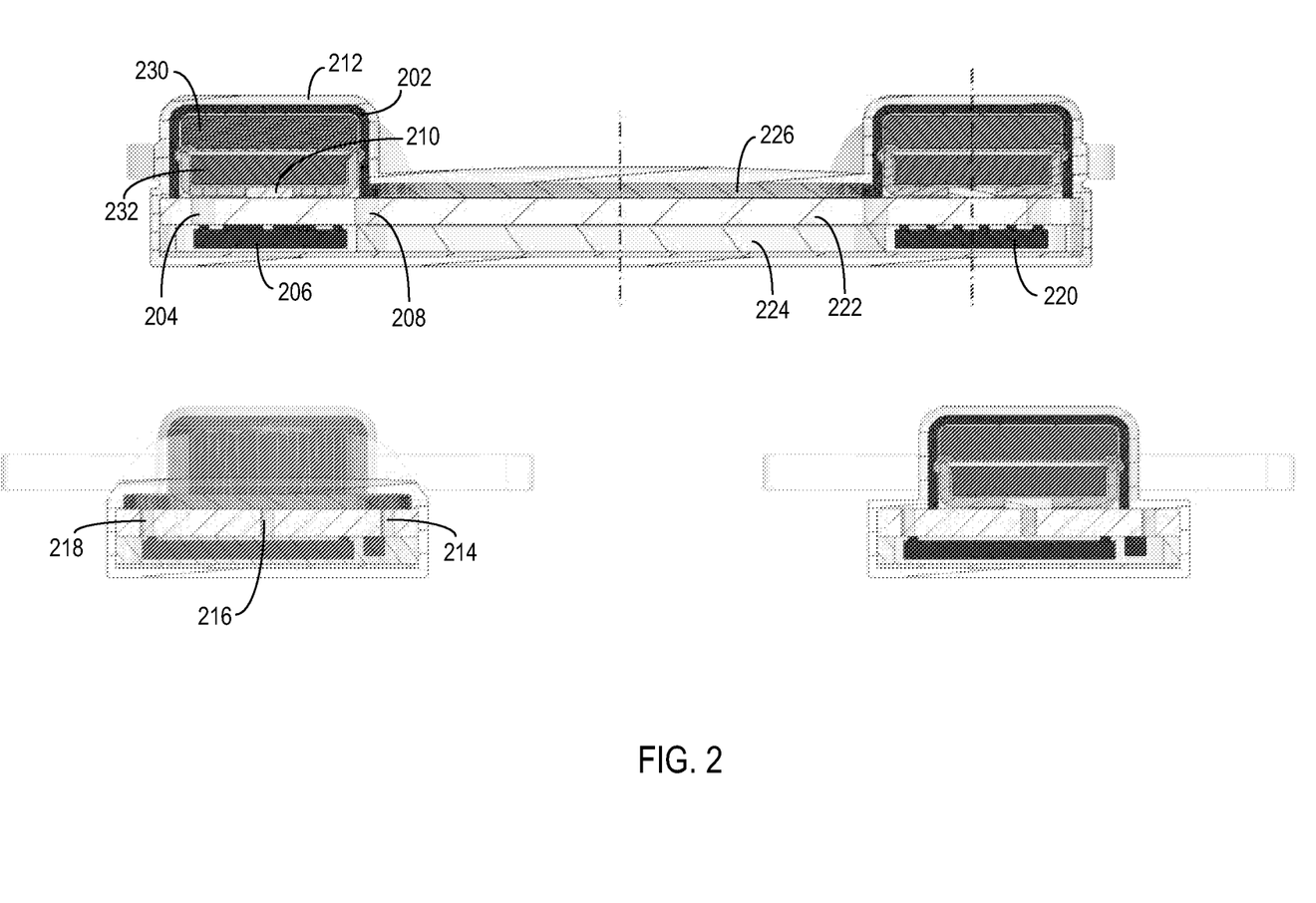
FIG. 2 is a side perspective view of an implantable ophthalmic device depicting feedthrough lines interconnecting power sources and an integrated circuit according to one embodiment.

Embodiments of the technology disclosed herein include an implantable ophthalmic device with a hermetically sealed feedthrough and a hermetically sealed cavity containing electronic devices such as a power source and a method for making such an implantable ophthalmic device. An illustrative implantable ophthalmic device is shown in FIG. 1 and FIG. 2 and includes a first wafer depicted in FIG. 1 as element 128 and in FIG. 2 as element 222. The first wafer may be made of a glass material according to one embodiment. According to one specific embodiment, the first wafer is made of borosilicate glass, such as Borofloat® 33, fused silica, and/or high index glasses such as high index glass types such as S-TIM22 or N-SF5, for example. The first wafer 128 may have multiple feedthrough apertures or channels 126 from a first side of the first wafer through to the second side of the first wafer according to one exemplary embodiment. The feedthrough channels may be filled with a conductive material to provide a conductive path for electrical communication from a first side of a first wafer to a second side of the first wafer.

Referring to FIG. 1, an exploded view of an electronics assembly 100 for an exemplary implantable ophthalmic device with feedthroughs 126 that are hermetically sealed to prevent leakage of foreign material from the device 100 into the eye. As defined herein, a hermetically sealed cavity or feedthrough is a cavity or feedthrough that passes an American Society for Testing and Materials (ASTM) E493/E493M-11 helium leak test with a leak rate of less than $5\times10^{-12}$ Pa $m^{-3}$ $S^{-1}$. The assembly 100 includes electronic components such as application specific integrated circuits (ASICs) 118 and 130.

Furthermore, additional electronic components may be disposed within the cavities shown in wafer 132. The side perspective view of device 100 shown in FIG. 2 depicts ASIC 206 within a cavity of intermediate wafer 222 according to another view. These cavities may be defined by sealing apertures in the wafer 132 between a first wafer 128 and a second wafer 134, which can be bonded together using laser fusion bonding, pressure bonding, anodic bonding and/or other various bonding techniques as described below. Other elements, such as coil 122, photovoltaic (PV) cell 124, and electrical lines 114 and 116 may be affixed to or sealed between the wafers.

In some embodiments, feedthrough channels 126 have a cylindrical or hourglass shape wherein a maximum diameter included in the hourglass shape reaches between about 100 µm to about 250 µm. According to some embodiments, the conductive material that fills the feedthrough channels 126 may be titanium, nickel, gold, iron, or an alloy thereof, to provide the conductive path that links the first and second sides of the first substrate. In some embodiments, alloys are to be developed to match the dilatation coefficient of the glass and hence avoid mechanical constraints due to temperature variations.

Feedthrough channels 126 may be coated or capped with the conductive material such that the conductive material has a thickness of about 10 µm to about 200 µm and/or a resistance of about 10 Ohms or less according to one embodiment. In some cases, the conductive material has a coefficient of thermal expansion (CTE) that is approximately equal to a CTE of the first wafer, e.g., the CTEs of the conductive material and the first substrate may be about 2.0 ppm to about 5.0 ppm, according to one exemplary embodiment. The conductive material is in electrical communication with the electronic component such as an application-specific integrated circuit processor (ASIC) 118 or 130, capacitor, memory, programmable logic analyzer, analog-to-digital converter, or a battery charger according to some embodiments.

Figure 4:
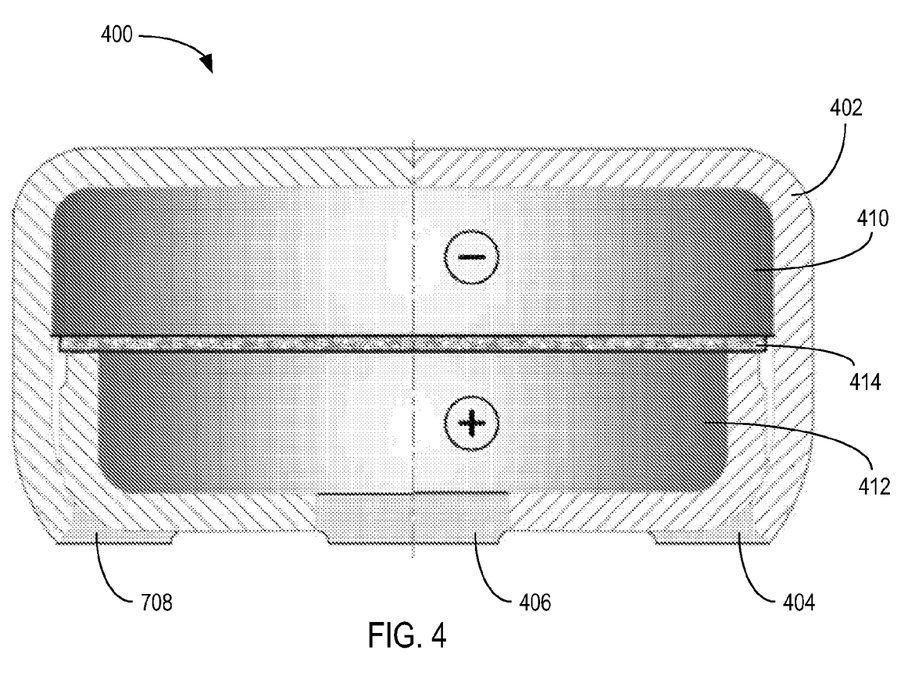
FIG. 4 is a side perspective view of one of the power sources used in the implantable ophthalmic device according to one embodiment.

For example, as shown in FIG. 2, feedthrough channels 204 and 208 provide an electrical connection from a battery with an anode 230 and a cathode 232 to an ASIC 206 with the first wafer 222 placed in between the battery and ASIC 206. The batteries 120, which may be rechargeable, include an anode 104 and cathode 108 held apart by a separator 106 and covered in a housing or can 102 to facilitate leakage protection. A battery casing cap 110 insulates the anode 104 and cathode 108 of the battery from the rest of the assembly 100. Feedthroughs 204, 208, 214 and 216 may be in electrical communication with the cathode 406 and anode 410 of battery 400 through electrical contacts 406 and 404, as shown in FIG. 4, according to one embodiment.

According to one embodiment, electrical contacts 404 and/or 408 are offset from feedthrough channels 204 and 206 such that a conductive electrical component (not shown) electrically connects electrical contacts 406 and 404 to selected feedthrough channel such as feedthrough channel 204 or 208, for example. Referring again to FIG. 4, electrical contacts 404 and 408 form a circular ring electrical contact surface while electrical contact 406 forms a solid circular electrical contact surface. According to one embodiment, electrical contact surfaces 408 and 406 are made with gold solder and a protective housing or can 402 surrounding at least a portion of the battery is made of a metal such as titanium and is covered with a non-conductive coating. According to some exemplary embodiments, the housing 402 is made of gold such as 24 karat gold, and a non-conductive coating is optionally applied thereon.

The assembly 100 also includes an inductive antenna coil 122 and a photovoltaic cell 124 that can be used to recharge batteries 102 and 120. The coil 122 and the photovoltaic cell 124 can also be used for wireless communication with external processors, e.g., to update and/or extract information store in memory on one or both of the ASICs 118 and 130. The photovoltaic cell 170 can also be used to detect accommodative triggers, changes in pupil diameter, and/or other physiological or environmental indications. In some examples, the coil 122 has about fifteen windings arranged about a perimeter of 5.1 mm×3.0 mm. The coil 122 and photovoltaic cell 124 may also be in electrical communication with the ASICs 118 and 130 via the feedthroughs 126.

For instance, a battery charger (not shown) in at least one of the ASICs 118 or 130 may control the recharging process as described in PCT/US20111040896 to Fehr et al., which is incorporated herein by reference in its entirety. Similarly, a processor in one of the ASICs 130 may receive signals from the photovoltaic cell 170 representing the pupil diameter as also described in PCT/US20111040896 to Fehr et al., which is incorporated herein by reference in its entirety. The processor may also control the diameter of an aperture defined by the electro-active cell 160 in response to signals from the photovoltaic cell 170, e.g., as described in U.S. Pat. No. 7,926,940 to Blum et al., which is also incorporated herein by reference in its entirety.

Fabrication of an electronics assembly, such as the one shown in FIG. 1, may begin with fabrication of a hermetically sealed feedthroughs 126. The feedthroughs 126 may be drilled into a substrate, etched into a substrate, or sand blasted into a substrate which is then cut or diced into individual wafers like the first wafer 128 shown in FIG. 1. Once the channels have been created, conductive material is deposited within the channels. According to one embodiment, depositing the conductive material is performed by galvanic growth or electrochemical deposition techniques. The conductive material may be a biocompatible material, such as gold. Alternatively, the conductive material may be a material, such as a nickel alloy (e.g., NiFe), whose coefficient of thermal expansion (CTE) can be selected to be about equal to (e.g., within 10% of) the CTE of the first wafer 128. If the conductive material 308 is not biocompatible, the inner surface of the channel may be coated or lined a biocompatible material to provide an extra layer of protection.

For example the channel 306 may be filled with conductive nickel, then both endings can be covered or lined with biocompatible titanium, or gold, or a combination thereof. Once deposited, the conductive material forms a conductive path that seals the channel and provides electrical communication from one side of a first wafer 222 to the other side of the first wafer 222. For example, feedthroughs 204 and 208 will provide electrical communication from anode 230 and cathode 232 of a battery to an ASIC 206 on the other side of first wafer 228. The electrical communication via feedthroughs 204 and 208 between a battery 400 and an ASIC 206 may be facilitated by placing conductive contacts, such as gold contacts on the surface of first wafer 228 such that they are in electrical and physical contact with battery contacts 408 and 406 and in electrical contact with feedthroughs 204 and 208, according to one example. The conductive contacts may be exposed and even with the surface of the first wafer 222 according to one exemplary embodiment. In a further embodiment, there will only be one conductive contact in physical contact with cathode contact 406 and only one conductive contact in physical contact with anode contact 408.

In designing a fully functional, biocompatible, mechanically reliable implantable ophthalmic device 100 with a predictable lifetime of use, several factors must be taken into consideration. In addition to providing a functional electrical connection through a feedthrough 126 between a power source such as a battery 120 and an ASIC 130, the implantable ophthalmic device 100 must also ensure such an electrical connection is mechanically reliable over a long period of time. Furthermore, ophthalmic device 100 must provide electrical separation between an electrical contact associated with the cathode of the battery 406 and an electrical contact associated with the anode of the battery 408. Additionally, various component parts shown in FIG. 1 must be securely and reliably bonded together in order to prevent both the ingress of fluid into cavities of implantable ophthalmic device 100 that contain electrical components such as battery 232 and ASIC 206, but also to prevent electro-active fluid, such as liquid crystal material, from leaking into the eye or surrounding tissue.

Figure 3:
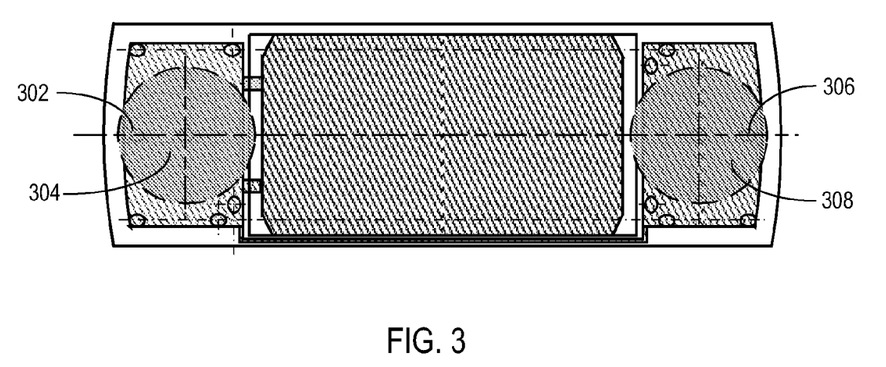
FIG. 3 is a top perspective view of the implantable ophthalmic device depicting the position of the power sources according to one embodiment.
Figure 5:
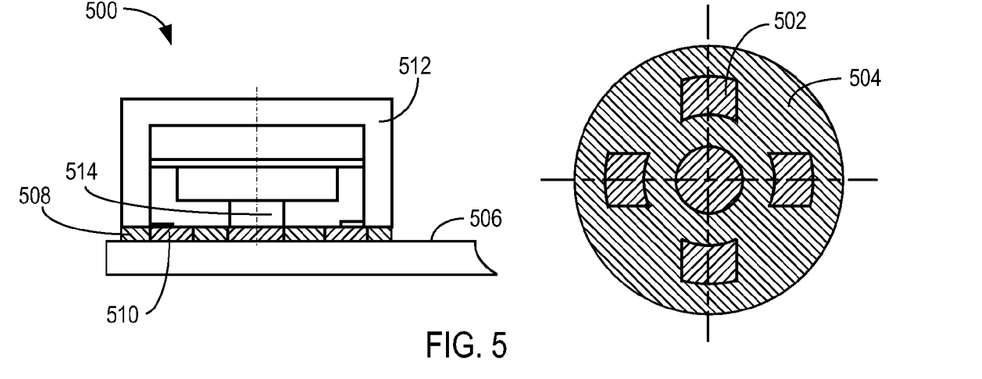
FIG. 5 is a side perspective view of a battery, an intermediate layer, and a first wafer according as well as a top perspective view of the intermediate layer according to one embodiment.

One exemplary solution to such design considerations is depicted in FIG. 5. FIG. 5 depicts a profile and top view perspective of one embodiment 500 for providing electrical connections and mechanical bonds between a battery, battery housing 412, and a first wafer 406. The battery shown in FIG. 5 may contains the properties of the battery shown in FIG. 4, according to one embodiment, with a cathode electrical contact 406 provided in a central region of the battery, and a circular anode electrical contact region represented in FIG. 4 by elements 404 and 408 surrounding the cathode electrical contact. For example, in FIG. 3, cathode electrical contacts for a given battery may be centered about position 308 or 304, while anode electrical contacts for a given battery may form a circular region intersecting positions 302 or 306

Referring again to FIG. 5, battery housing 512 forms a sealed cavity for a battery with a first wafer 506. The cavity may be sealed and mechanically bonded together using several techniques alone or in combination including but not limited to fusion bonding, pressure bonding, anodic bonding, conductive glue bonding, laser fusion bonding, cold welding, ultrasonic welding, inductive welding, or laser welding. The aforementioned techniques may provide hermetically sealed, airtight, or otherwise enclosed cavities to prevent the ingress and egress of fluid or other elements with respect to cavities holding electronics or providing electrical connections between various electronic components.

According to one embodiment, an intermediate layer including sections 508 and 510 may facilitate an electrical connection between a battery in housing 512 and an electrical component such as an ASIC (not shown) below the surface of the first wafer 406 according to one exemplary embodiment. The intermediate layer may also at least partially facilitate a mechanical bonding between housing 512 and a first wafer 506 according to one embodiment. The intermediate layer can be made out of a non-conductive material, but not limited to, ceramic such as Al2O3, peak, anodized titanium, glass coated gold, non-conductive glue and a conductive material, but not limited to, gold, conductive glue or other metallic alloys. According to the embodiment depicted in FIG. 5, the five cavities 502 are aligned with electrical contacts of the battery such as electrical contact 514. As described previously with respect to FIG. 4, the battery may include a central circular electrical contact 406 and a second, ring shaped electrical contact defined by elements 408 and 404. Accordingly, the cavities 502 may be aligned with these electrical contacts to facilitate electrical communication. Furthermore, cavities 502 facilitate electrical communication between the battery and an ASIC (not shown) below the first wafer 506 by filling them with a film of conductive glue. The cavities of conductive glue also provide additional mechanical bonding to facilitate a sealed environment for electronic components such as the battery shown in FIG. 5. In addition to conductive glue, the intermediate layer may also comprise a gasket 504 that are cut so as to define cavities 502. According to one embodiment gasket 504 is made of a ceramic material and defines a sealed cavity with first wafer 506 around the battery.

Figure 6:
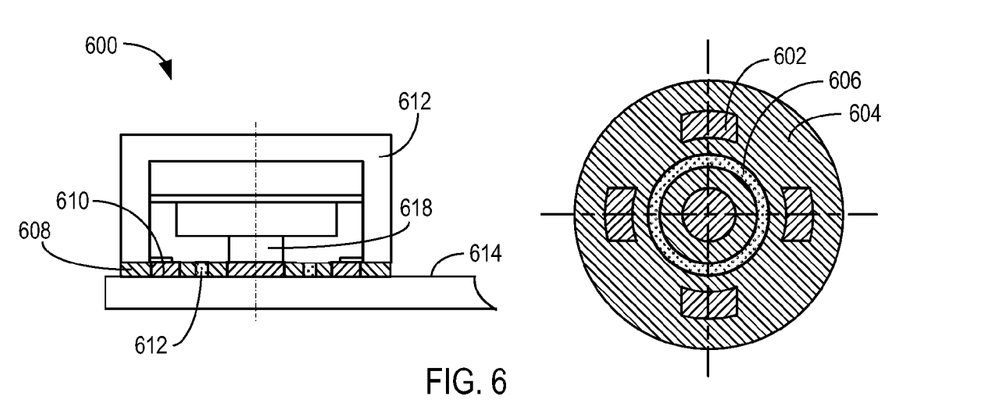
FIG. 6 is a side perspective view of a battery, an intermediate layer, and a first wafer according as well as a top perspective view of the intermediate layer according to another embodiment.

According to another exemplary embodiment depicted in FIG. 6, the intermediate layer as shown in FIG. 5 including a conductive glue 502 and a ceramic gasket 504 portions further includes a hydrophobic barrier as shown by elements 606 and 612 positioned between the central conductive glue segment of the intermediate layer electrically connected with an anode of the battery and the conductive glue segments electrically connected with a cathode of the battery. The hydrophobic barrier 606, prevents ion leakage between the anode and cathode portions of the battery in order to facilitate a longer battery life. The hydrophobic barrier 606 may be an etched ring filled with silicon oil or realized through a specific hydrophobic glass wafer and a battery surface treatment, according to one embodiment.

Figure 7:
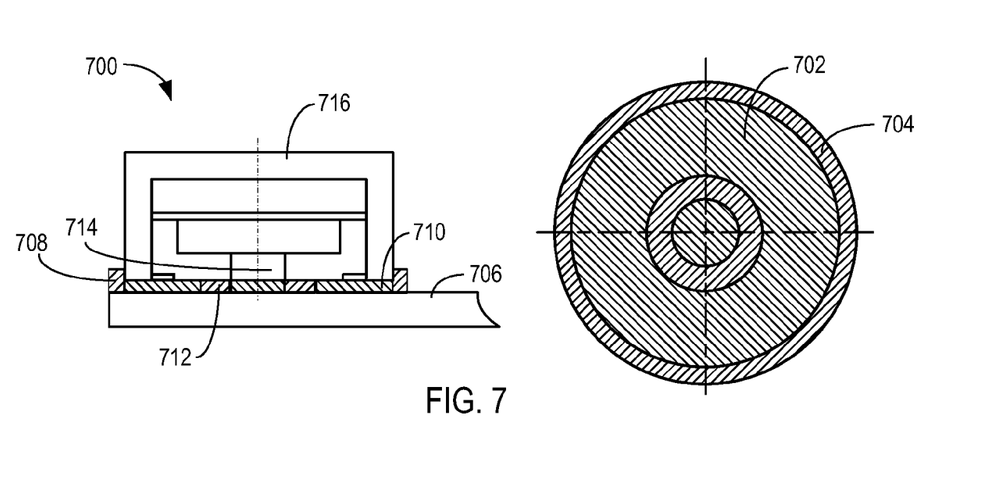
FIG. 7 is a side perspective view of a battery, an intermediate layer, and a first wafer according as well as a top perspective view of the intermediate layer according to another embodiment.

According to another exemplary embodiment 700, depicted in FIG. 7, the intermediate layer includes two segments of conductive glue 702 and two segments of a glass formation or other isolated material 704. The glass formation or other isolated material may include a raised edge 708 to hold battery housing 716 onto a first wafer 706. The glass formation may be made according to a glass growth process that is carried out on the surface of first wafer 706. If raised edge 708 is an isolated material other than a glass formation, the isolated material may be coated with an SiO2 coating, according to one exemplary embodiment. As in FIGS. 5 and 6, the conductive glue portions associated with the electrical contacts of the battery such as contact 714 facilitate an electrical connection between a battery in housing 716 and an electrical component such as an ASIC (not shown) below the surface of the first wafer 706.

Figure 8:
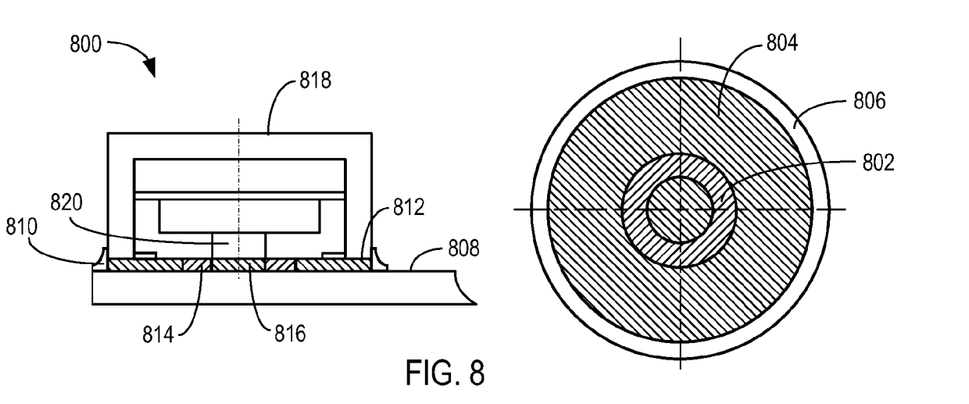
FIG. 8 is a side perspective view of a battery, an intermediate layer, and a first wafer according as well as a top perspective view of the intermediate layer according to another embodiment.

According to another exemplary embodiment 800, depicted in FIG. 8, the intermediate layer includes three different types of materials. A first material includes two segments of conductive glue 804 associated with the electrical contacts of the battery such as contact 820 facilitate an electrical connection between a battery in housing 818 and an electrical component such as an ASIC (not shown) below the surface of the first wafer 808. The two segments of conductive glue are also depicted as elements 816 and 812 in the side perspective view shown in FIG. 8. The intermediate layer also includes a sealing ring 802 and 814, used to provide mechanical support for electrical connections and to facilitate bonding or adherence of the housing 818 to the surface of the first wafer 808. A third element of the intermediate layer is a bio-compatible glue 806 and 810, formed around the perimeter of the battery housing 818 to form a sealed cavity between the housing 818 and the first wafer 808. The bio-compatible glue can assist in increasing the strength of the mechanical connection between the housing 818 and the first wafer 808 as well as improving the sealing and electrical insulation of the cavity formed by housing 818 and first wafer 808.

Figure 9:
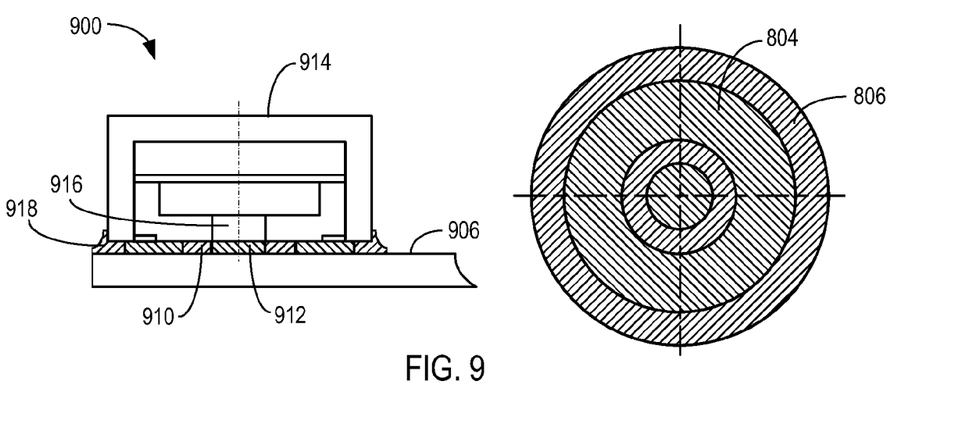
FIG. 9 is a side perspective view of a battery, an intermediate layer, and a first wafer according as well as a top perspective view of the intermediate layer according to another embodiment.

According to another exemplary embodiment 900, depicted in FIG. 9, the intermediate layer includes segments of gold coating 912 and 902. The segments of gold coating are associated with the electrical contacts of the battery such as contact 916 to facilitate an electrical connection between a battery in housing 914 and an electrical component such as an ASIC (not shown) below the surface of the first wafer 906. The intermediate layer also includes as segments of glue 904 and 910, such as bio-compatible glue, for example. The bio-compatible glue can assist in increasing the strength of the mechanical connection between the housing 914 and the first wafer 906 as well as improving the sealing and electrical insulation of the cavity formed by housing 914 and first wafer 906. In the embodiment disclosed in FIG. 9, the battery contacts such as cathode contact 916 may be made of gold. The gold coating 902 may be bonded with the anode and cathode gold battery contacts according to compression bonding, anodic bonding, or a welding process such as cold welding, ultrasonic welding, inductive welding, or laser welding. In addition, the compression bonding may include different types of compression bonding such as thermo-compression bonding where compression takes place at temperatures above room temperature in order to facilitate a stronger bond.

According to one exemplary embodiment, compression bonding is used to bond the gold electrical contacts of battery to the gold coating 902. Under compression bonding, the compression causes the gold coating 902 in the intermediate layer to soften and adhere to the anode and cathode gold contacts of the battery as is shown by elements 406 and 404 in FIG. 4. Using the compression bonding process, temperatures can be kept under 300° C., which is a critical temperature for certain components disposed on or between the wafers. Accordingly, compression bonding is an advantageous bonding technique according to some embodiments.

Figure 10:
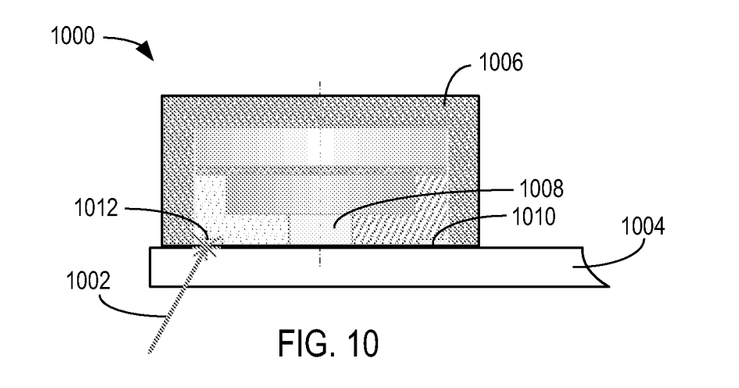
FIG. 10 is a side perspective view of a battery and a first wafer according to another embodiment.

According to another exemplary embodiment 1000, depicted in FIG. 10, the electrical contacts of the battery 1012, 1010, and 1008 may be bonded according to a laser welding bonding process. Under this exemplary process, a mechanical and electrical bond can be formed with a first wafer 1004 using a focused laser beam to weld the electrical contacts, optionally with a metallic coating deposited on the first wafer 1004, together with the battery housing. Laser fusion bonding, or laser welding, is particularly attractive because it involves heating only those specific areas of wafer 1004 with the battery or battery housing. As a result, the components attached to and/or disposed between the wafers do not heat up during the fusion process. In addition, to bonding metals is in discussed previously with respect to FIG. 10, laser fusion bonding can be used to bond one piece of glass directly to another piece of glass (i.e., without layers between the pieces of glass), which eliminates additional materials and deposition steps. Accordingly, in FIG. 10, if housing 1006 and first wafer 904 are both made of glass, a laser welding or bonding process may be used.

More specifically, in the laser fusion bonding process, two like elements such as a glass housing 1006 and a glass wafer 1004 are held in contact with each other, and a beam from an ultrafast, ultraviolet laser is focused at or near the interface between the two like elements. The laser emits picosecond or femtosecond pulses of light that heat the wafers, which causes the elements to melt or fuse together. Scanning the pulsed laser beam in a closed loop along (or just inside) the edges of housing 1006 and wafer 1004, for example, creates a hermetically sealed cavity for electronics such as a battery or ASIC. The pulsed laser beam can also be scanned in multiple closed loops to create additional hermetically sealed areas within the perimeter of the wafers. For example, an ASIC 118 may be sealed in a cavity, which itself is sealed within the perimeter of the device 100.

Figure 11A:
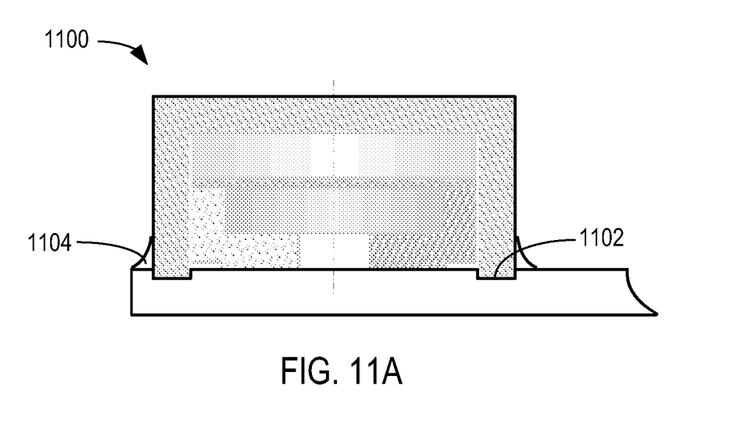
FIG. 11A is a side perspective view of a battery and a first wafer according to another embodiment.
Figure 11B:
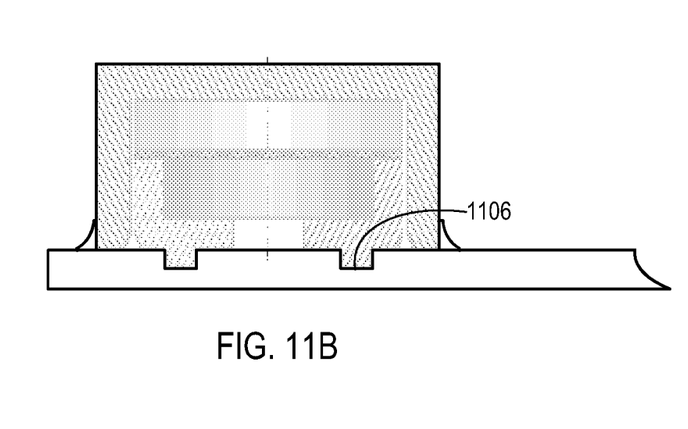
FIG. 11B is a side perspective view of a battery and a first wafer according to another embodiment.

According to another exemplary embodiment 1100, depicted in FIGS. 11A and 11B, a sealed cavity for the battery is achieved by etching position grooves 1102 on a first side of a first wafer. Subsequently, the housing of the battery can be placed in appropriately sized position grooves to form a sealed cavity. In addition, bio-compatible glue may be placed along the perimeter of the housing and the surface of the wafer to provide more robust mechanical bonding and sealant properties. Alternatively, as shown in FIG. 11B, the placement of etching grooves 1106 may be placed in various positions. With respect to the electrical connection between the battery and an ASIC below a first wafer, the connection may be formed by filling feedthroughs 126 with metallic solder, according to one embodiment.

Figure 12A:
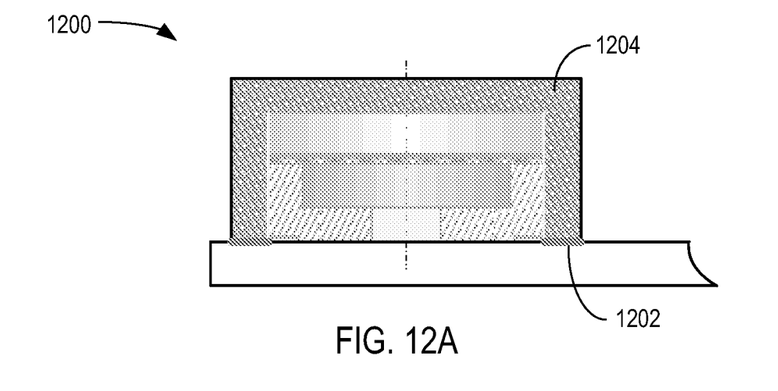
FIG. 12A is a side perspective view of a battery and a first wafer according to another embodiment.
Figure 12B:
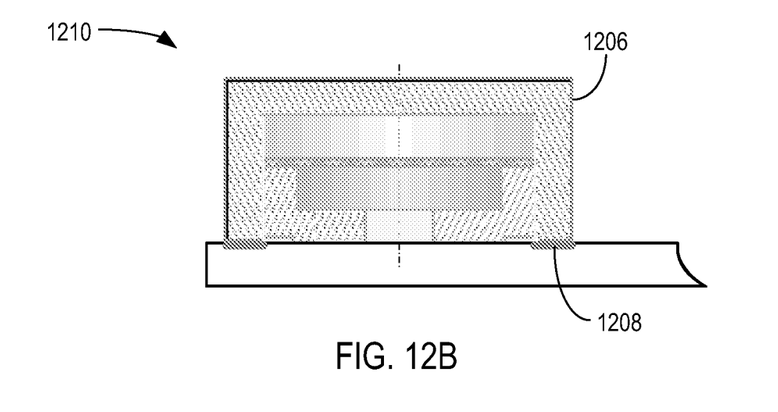
FIG. 12B is a side perspective view of a battery and a first wafer according to another embodiment.

According to another exemplary embodiment 1200 depicted in FIG. 12A, both the housing 1204 and the first wafer are made of glass so that laser fusion bonding technique can be used to form a hermetically sealed cavity for the battery. Alternatively, the housing 1206 may be made of a material other than glass such as metal or a ceramic that is coated with a glass coating of greater than 10 µm in order to use a laser fusion bonding process. With respect to the electrical connection between the battery and an ASIC below a first wafer, the connection may be formed by filling feedthroughs 126 with metallic solder, according to one embodiment.

Figure 13:
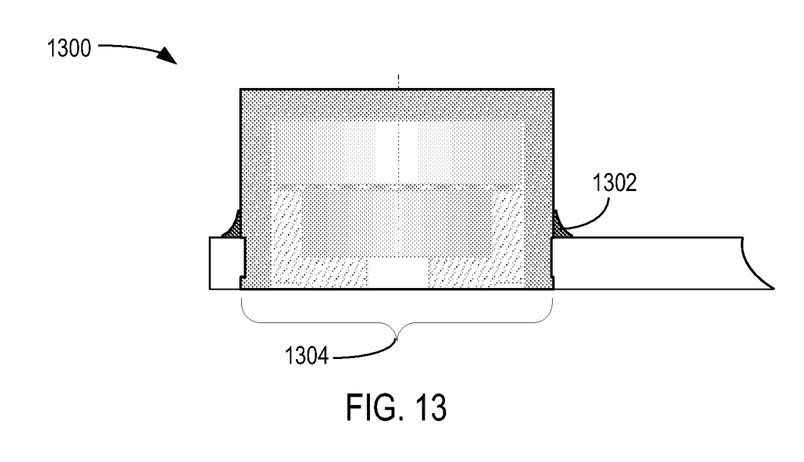
FIG. 13 is a side perspective view of a battery and a first wafer according to another embodiment.
Figure 14A:
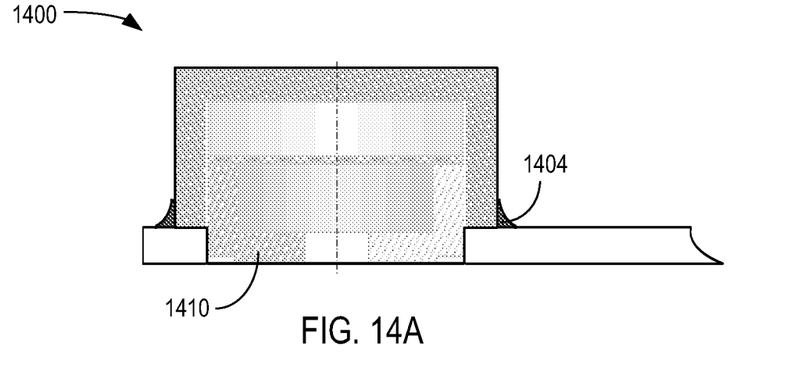
FIG. 14A is a side perspective view of a battery and a first wafer according to another embodiment.
Figure 14B:
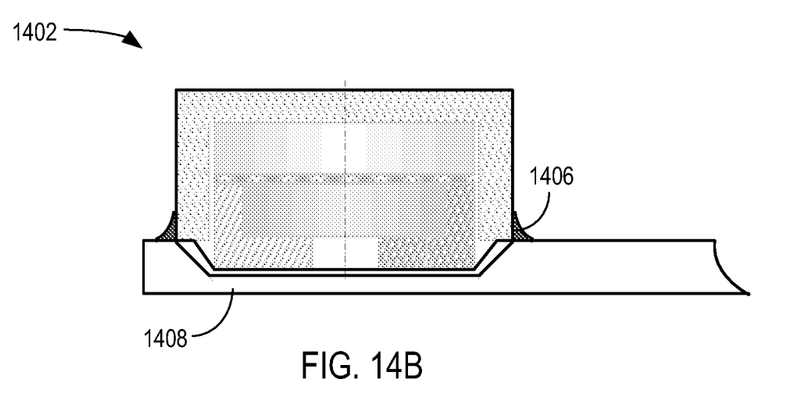
FIG. 14B is a side perspective view of a battery and a first wafer according to another embodiment.

According to another exemplary embodiment 1300 depicted in FIG. 13, the electrical contact portions of the battery are directly connected to an electrical circuit positioned below the first wafer. In addition, a sealed cavity may be formed between the housing and first wafer by placing a battery lid within a gap 1304 machined or etched into the first wafer. The cavity may further be sealed by a lining the perimeter of the housing and a surface of the first wafer with a bio-compatible glue 1302. FIGS. 14A and 14B depict additional exemplary embodiments for placing a battery protrusion or battery lid within a recess or cavity 1404, 1406 of a first wafer.

Figure 15:
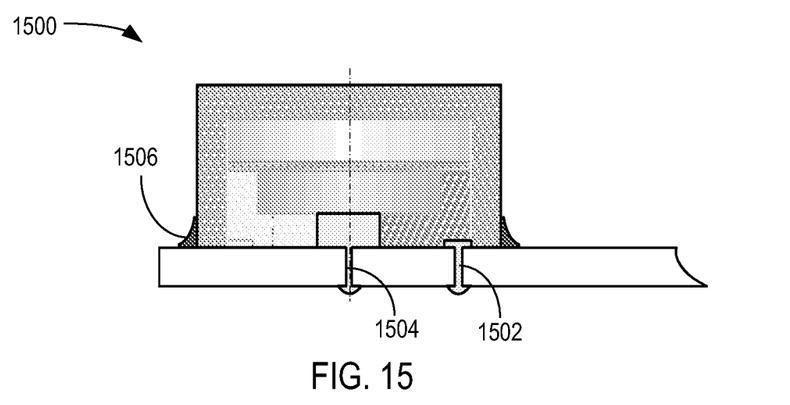
FIG. 15 is a side perspective view of a battery and a first wafer according to another embodiment.
Figure 16:
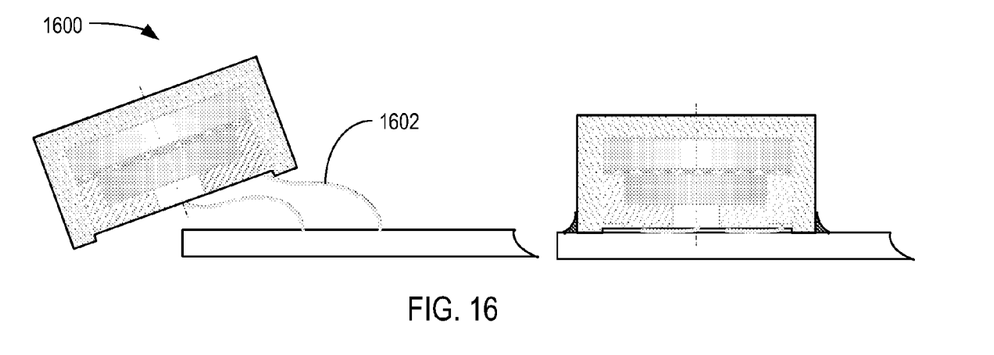
FIG. 16 is a side perspective view of a battery and a first wafer according to another embodiment.

With respect to FIG. 15, the electrical contact portions are electrically connected to an integrated circuit below the first wafer through conductive rivets 1502 and 1504 such that the rivet provides an electrical connection and is also used to bond the battery to the surface of the first wafer. Furthermore, the cavity containing the battery may further be sealed by lining the perimeter of the housing and a surface of the first wafer with a bio-compatible glue 1506. With respect to FIG. 16, the electrical contact portions of the battery are electrically connected to the integrated circuit through coated wiring 1602 and the bond between the first wafer and the housing comprises adhering the perimeter of the housing and a surface of the first wafer with a bio-compatible glue.

Figure 17:
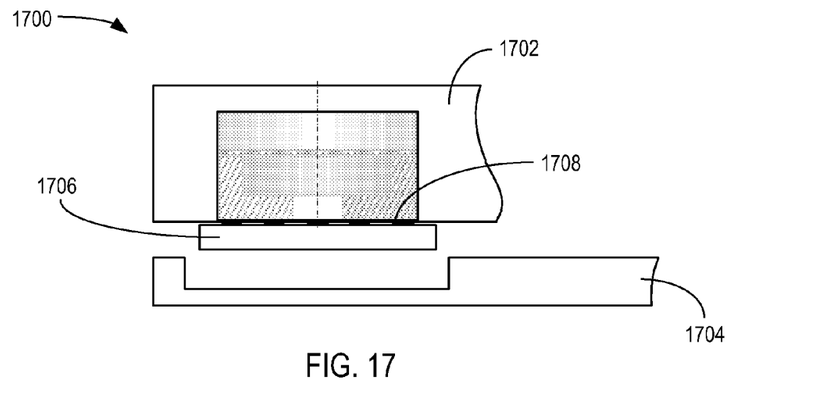
FIG. 17 is a side perspective view of a battery, an integrated circuit electronically coupled to the first battery, and a first wafer according to one embodiment.

With respect to system 1700 depicted in FIG. 17, the housing surrounding the battery is replaced with the first wafer 1702 that has been machined on a second side to form a sealed surface around the battery. In the embodiment shown in FIG. 17, the electrical contact portions 1708 are directly connected to the electrical circuit 1706. Furthermore, the electrical circuit 1706 is housed in a cavity machined into a second wafer 1704. The first and second wafer may form a sealed cavity for the electronics contained therein using a laser fusion bonding process.

Figure 18:
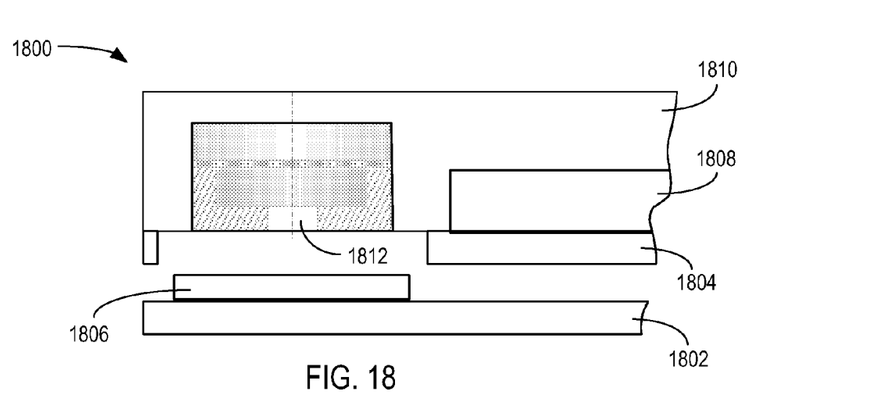
FIG. 18 is a side perspective view of a battery, an integrated circuit electronically coupled to the first battery, a first wafer, according to another embodiment.

With respect to the embodiment 1800 depicted in FIG. 18, a cavity 1808 for an inductive coil 122 is also provided. Embodiment 1800 includes a first wafer 1810, having a first cavity that a battery is inserted into as well as a second wafer 1804 bonded to the first wafer 1810 using a laser fusion bonding process such that the first wafer and the second wafer form a hermetically sealed cavity around the battery. Embodiment 1800 also includes an electronic circuit 1806 that is directly connected to the electrical contact portions of the battery such as cathode contact portion 1812. According to one embodiment, the integrated circuit is inserted into a gap in second wafer 1804 and an inductive coil 122 is inserted into a second cavity 1808 of the first wafer wherein the inductive coil is placed on a surface of the third wafer 1802.

Figure 19:
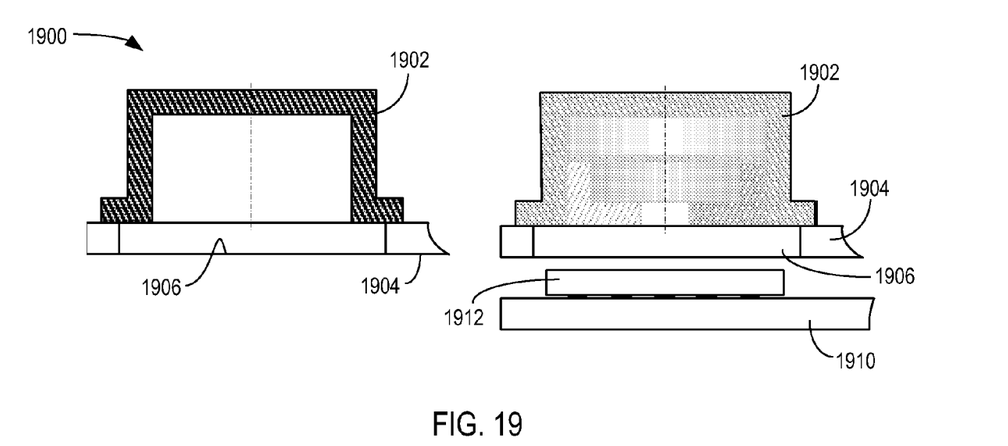
FIG. 19 is a side perspective view of a battery, an integrated circuit electronically coupled to the first battery, a first wafer, according to another embodiment.

With respect to embodiment 1900 depicted in FIG. 19, a gap is machined in the first wafer 1904 so that an integrated circuit 1912 is fit within the gap. Furthermore, housing 1902 is preferably metallic so that adhering the perimeter of the housing 1902 and a surface of the first wafer 1904 may be performed using one of a anodic bonding process and a high temperature bonding process prior to adhering the first wafer to the second wafer using a laser fusion process.

Under an anodic bonding technique, one of the glass wafers to be bonded is coated with a thin layer of silicon, polysilicon, tantalum, titanium, aluminum, and/or SiNx to form a coated glass wafer. The coated wafer is then cleaned (e.g., with isopropanol) and dried (e.g., with nitrogen gas), then aligned with housing 1902 between a top tool and a chuck which are connected to a voltage source. Setting the voltage of the voltage source to several hundred volts causes current to flow from the chuck to the top tool via the coated glass wafer 1904 and housing 1902. The current flow causes cations (e.g., alkali ions) in the coated glass wafer 1904 to drift towards the top tool, which acts as a cathode, and anions in the glass wafers to drift towards the chuck, which acts as an anode. As a result, the region of the housing 1902 becomes depleted of cations, and the region of the coated glass wafer 1904 on the other side of the coating becomes depleted of anions. This depletion causes the surfaces of the housing 1902 and coated glass wafer 1904 bordering the coating to become highly reactive, which leads to the formations of a solid chemical bond between the wafer 1904 and the housing 1902.

Figure 20:
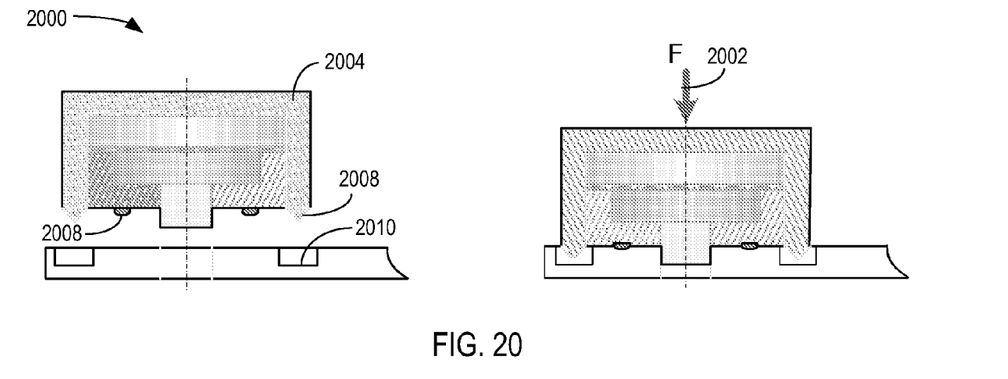
FIG. 20 is a side perspective view of a battery and a first wafer according to one embodiment.

With embodiment 2000 depicted in FIG. 20, portions of the housing 2004 are coated with a film of conductive material such as gold 2008 and the bond between the first wafer and the housing is formed by a cavity 2010 in a surface of the first wafer filled with conductive material such as gold according to one embodiment. According to one embodiment, the gold coated portions of the housing 2008 are adhered to the cavity 2010 using a cold weld process according to one exemplary embodiment. For various welding and bonding processes it is required that the film of conductive material 2008 and the conductive material filling gap 2010 be the same material for proper bonding. Once the wafer and battery housing are bonded to form a sealed cavity to form assemblies, the assemblies may be encapsulated in acrylic or any other suitable material 136.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations.

However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A system for electrically and mechanically connecting components of an implantable ophthalmic device to provide a bio-compatible sealing to prevent the ingress of fluid and the egress of battery fluids comprising:
    at least one battery with a surface comprising electrical contact portions;
    a housing for the at least one battery;
    a first wafer bonded to the housing, wherein each of the at least one battery is positioned towards a side of the first wafer, and wherein the housing and the first wafer form a sealed surface around the at least one battery; and
    an electronic circuit electrically connected to the electrical contact portions of the battery.

2. The system of claim 1, wherein the electrical contact portions are electrically connected to the electronic circuit through conductive glue and the bond between the first wafer and the housing comprises adhering at least one of the battery and the housing to a surface of the first wafer with a gasket.

3. The system of claim 2, further comprising a hydrophobic barrier positioned between conductive glue electrically connected with an anode of the battery and conductive glue electrically connected with a cathode of the battery to prevent ion leakage.

4. The system of claim 3, wherein the hydrophobic barrier comprises silicon oil.

5. The system of claim 2, wherein the gasket portion is formed into concentric rings separated by the conductive glue such that an outer ring gasket portion is formed around the perimeter of the housing and an inner ring gasket portion is contained within the housing.

6. The system of claim 2, wherein the gasket is comprised of one of ceramic or glass.

7. The system of claim 2, wherein the sealed surface around the battery is hermetically sealed.

8. The system of claim 1, wherein the electrical contact portions are electrically connected to the electronic circuit through conductive glue and the bond between the first wafer and the housing comprises:
    a sealing ring contained within the housing; and
    adhering the perimeter of the housing and a surface of the first wafer with a bio-compatible glue.

9. The system of claim 1, wherein the electrical contact portions are made of a conductive material, the conductive material electrical contact portions are electrically connected to the electronic circuit through a conductive material coating and the bond between the first wafer and the housing comprises:
    adhering at least one of the housing and battery to a surface of the first wafer with a bio-compatible glue; and
    bonding the conductive material coating to the conductive material electrical contacts of the battery using a welding process.

10. The system of claim 1, wherein the electrical contact portions are electrically connected to the electronic circuit through solder and the bond between the first wafer and the housing comprises:
    grooves in a surface of the first wafer so that a portion of at least one of the battery or housing is positioned within the etched grooves; and
    adhering the perimeter of the housing and a surface of the first wafer with a bio-compatible glue.

11. The system of claim 1, wherein the housing is comprised of glass, the electrical contact portions are electrically connected to the electronic circuit through solder, and the bond between the first wafer and the housing comprises adhering the glass housing to a surface of the first wafer using a laser fusion process.

12. The system of claim 1, wherein the housing is coated with a wafer compatible glass coating wherein the glass coating has a thickness greater than 10 micrometers and the bond between the first wafer and the housing comprises adhering the glass coated housing to a surface of the first wafer using a laser fusion process.

13. The system of claim 1, wherein the electrical contact portions are directly connected to the electronic circuit and the bond between the first wafer and the housing comprises:
 a gap in the first wafer so that the perimeter of the housing is fit within the gap; and
 adhering the perimeter of the housing and a surface of the first wafer with a bio-compatible glue.

14. The system of claim 1, wherein the electrical contact portions are directly connected to the electronic circuit and the bond between the first wafer and the housing comprises:
 a gap in the first wafer so that the perimeter one of battery lid and a protrusion of the battery lid is fit within the gap; and
 adhering the perimeter of the housing and a surface of the first wafer with a bio-compatible glue.

15. The system of claim 1, wherein the electrical contact portions are electrically connected to the electronic circuit by feeding an electrical connection through the first wafer and the bond between the first wafer and the housing comprises:
 a cavity in a surface of the first wafer so that a battery lid is recessed within the cavity;
 adhering the perimeter of the housing and a surface of the first wafer with a bio-compatible glue; and
 adhering an electrical contact of the battery associated with and anode of the battery to the first wafer using a welding process.

16. The system of claim 1, wherein the electrical contact portions are electrically connected to the electronic circuit through a rivet and the bond between the first wafer and the housing comprises:
 the rivet used as an electrical connection; and
 adhering the perimeter of the housing and a surface of the first wafer with a bio-compatible glue.

17. The system of claim 1, wherein the electrical contact portions are electrically connected to the electronic circuit through coated wiring and the bond between the first wafer and the housing comprises adhering the perimeter of the housing and a surface of the first wafer with a bio-compatible glue.

18. The system of claim 1, wherein the housing is metallic, the electrical contact portions are directly connected to the electronic circuit wherein the integrated circuit is in contact with a second wafer and the bond between the first wafer and the housing comprises:
 a gap in the first wafer so that electronic circuit is fit within the gap; and
 adhering the perimeter of the metallic housing and a surface of the first wafer using one of a anodic bonding process and a high temperature bonding process prior to adhering the first wafer to the second wafer using a laser fusion process.

19. The system of claim 1, wherein portions of the housing a coated with a film of gold and the bond between the first wafer and the housing comprises:
 a cavity in a surface of the first wafer comprising gold wherein the gold coated portions of the housing are adhered to the cavity using a cold weld process; and
 adhering an electrical contact of the battery to the first wafer with glue.

20. The system of claim 1, wherein the first wafer is glass.

21. The system of claim 9, wherein the conductive material is gold.

22. The system of claim 1, wherein the electrical contact portions are made of a conductive material, the conductive material electrical contact portions are electrically connected to the electronic circuit through a conductive material coating and the bond between the first wafer and the housing comprises:
 adhering at least one of the housing and battery to a surface of the first wafer with a bio-compatible glue; and
 bonding the conductive material coating to the conductive material electrical contacts of the battery using thermo-compression bonding.

23. The system of claim 1, wherein the electrical contact portions are electrically connected to the electronic circuit through solder and the bond between the first wafer and the housing comprises:
 grooves in a surface of the first wafer so that a portion at least one of the battery or housing is positioned within the etched grooves; and
 adhering the perimeter of the housing and a surface of the first wafer by welding the housing to the surface of the first wafer.

24. The system of claim 11, wherein the laser fusion process is enhanced by a light absorption layer, such as for example chromium or titanium, deposited between the first wafer and the housing.

25. The system of claim 12, wherein the laser fusion process is enhanced by a light absorption layer, such as for example chromium or titanium, deposited between the first wafer and the housing.

26. The system of claim 1, wherein the electronic circuit is electrically connected to the electrical contact portions of the battery through at least one hourglass shaped feedthrough channel formed in the first wafer wherein the hourglass shaped feedthrough channel comprises a conductive material.

27. A system for electrically and mechanically connecting components of an implantable ophthalmic device to provide a bio-compatible sealing to prevent the ingress of fluid and the egress of battery fluids comprising:
 at least one battery with a surface comprising electrical contact portions;
 at least one first wafer having a first cavity into which at least one of the at least one battery is inserted;
 a second wafer bonded to the first wafer using a laser fusion bonding process such that the first wafer and the second wafer form a sealed surface around the at least one of the at least one battery, and such that the at least one of the at least one battery is positioned towards a side of the second wafer; and
 an electronic circuit that is directly connected to the electrical contact portions of the battery wherein the electronic circuit is inserted into a cavity of the second wafer.

28. A system for electrically and mechanically connecting components of an implantable ophthalmic device to provide a bio-compatible sealing to prevent the ingress of fluid and the egress of battery fluids comprising:
 at least one battery with a surface comprising electrical contact portions;
 a first wafer having a first cavity the at least one battery is inserted into;

a second wafer bonded to the first wafer using a laser fusion bonding process such that the first wafer and the second wafer form a sealed surface around the at least one battery, and the at least one battery is positioned towards a side of one of the first wafer and the second wafer;

an electronic circuit that is directly connected to the electrical contact portions of the battery wherein the electronic circuit is inserted into at least one of a gap in a third wafer and in a cavity of the second wafer; and an inductive coil inserted into at least one of a second cavity of the first wafer and a cavity of the second wafer wherein the inductive coil is placed on a surface of the third wafer.

29. A method of manufacturing an implantable ophthalmic device to provide a bio-compatible sealing to prevent the ingress of fluid and the egress of battery fluids comprising:

placing at least one battery with a surface comprising electrical contact portions into a housing;

bonding the housing with a first wafer such that the housing and the first wafer form a sealed surface around the at least one battery towards one side of the first wafer; and placing the first wafer in a position such that an electronic circuit is electrically connected to the electrical contact portions of the battery.

30. The method of claim 29, wherein the sealed surface around the battery is a hermetically sealed surface.

31. A method of manufacturing an implantable ophthalmic device to provide a bio-compatible sealing to prevent the ingress of fluid and the egress of battery fluids comprising:

inserting a battery with a surface comprising electrical contact portions into a first cavity towards one side of a first wafer;

bonding a second wafer to the first wafer using a laser fusion bonding process such that the first wafer and the second wafer form a sealed surface around the battery;

connecting an electronic circuit directly to the electrical contact portions of the battery; and inserting the electronic circuit into a cavity of the second wafer.

32. A method of manufacturing an implantable ophthalmic device to provide a bio-compatible sealing to prevent the ingress of fluid and the egress of battery fluids comprising:

inserting a battery with a surface comprising electrical contact portions into a first cavity of a first wafer;

bonding the first wafer to a second wafer using a laser fusion bonding process such that the first wafer and the second wafer form a sealed surface around the battery, and the battery is positioned towards a side of at least one of the first wafer or the second wafer;

connecting directly an electronic circuit to the electrical contact portions of the battery; inserting the electronic circuit into a gap in a third wafer; and inserting an inductive coil into a at least one of a second cavity of the first wafer and a cavity of the second wafer wherein the inductive coil is placed on a surface of the third wafer.

\* \* \* \* \*